(12) United States Patent
Suzuki

(10) Patent No.: US 6,718,983 B1
(45) Date of Patent: Apr. 13, 2004

(54) CONDOM

(75) Inventor: Michio Suzuki, Ryugasaki (JP)

(73) Assignee: Okamoto Industries, Inc. (JP)

( * ) Notice: Subject to any disclaimer, the term of this patent is extended or adjusted under 35 U.S.C. 154(b) by 0 days.

(21) Appl. No.: 10/149,327

(22) PCT Filed: Oct. 27, 2000

(86) PCT No.: PCT/JP00/07576

§ 371 (c)(1),
(2), (4) Date: Jun. 5, 2002

(87) PCT Pub. No.: WO01/41682

PCT Pub. Date: Jun. 14, 2001

(30) Foreign Application Priority Data

Dec. 6, 1999 (JP) .............................. 11-346922
Dec. 6, 1999 (JP) .............................. 11-346923

(51) Int. Cl.$^7$ ................................. A61F 6/04
(52) U.S. Cl. ........................ 128/844; 128/918
(58) Field of Search ............... 128/842, 844, 128/918; 604/347–353

(56) References Cited

U.S. PATENT DOCUMENTS 5,829,440 A * 11/1998 Broad .................. 128/842

FOREIGN PATENT DOCUMENTS

| EP | 0 407 551 | 4/1995 | ............. A61F/6/04 |
| JP | 63-195823 | 12/1988 | ............. A61F/5/43 |
| JP | 2-33765 | 9/1990 | ............. A61F/6/04 |
| JP | 3-505173 | 11/1991 | ............. A61F/6/04 |
| JP | 5-65316 | 8/1993 | ............. A61F/6/04 |
| JP | 8/56978 | 3/1996 | ............. A61F/6/04 |
| JP | 3029333 | 7/1996 | ............. A61F/6/04 |
| JP | 9-132249 | 5/1997 | ............ B65D/33/00 |
| JP | 10-510452 | 10/1998 | ............. A61F/6/04 |
| JP | 11-019110 | 1/1999 | ............. A61F/6/04 |
| WO | 90/08522 | 8/1990 | ............. A61F/6/04 |
| WO | WO 92/20595 | * 11/1992 | |
| WO | 96/38107 | 12/1996 | ............. A61F/6/04 |

* cited by examiner

*Primary Examiner*—Michael A. Brown
(74) *Attorney, Agent, or Firm*—Schweitzer Cornman Gross & Bondell LLP

(57) ABSTRACT

A condom which can be fitted onto a penis without requiring for fingers to touch the penis and a condom body when in use, and which preferably does not admit the entry of air during fitting and is free from remnant air after fitting, wherein extension portions (5) of a specified length are ensured on a fitting tape (B) rolled up along with the condom body (A), and the condom body can be stored in a package (C) without this length being increased nor decreased during a packaging process.

12 Claims, 9 Drawing Sheets

CONDOM

TECHNICAL FIELD

This invention relates to a condom, and more specifically, to a condom which can be fitted without the fingers touching the penis or the condom body, to a condom which is easy to fit and air does not enter when the condom is to be fitted, and to a condom wherein air does not enter or remain in a sperm retention part or the vicinity of the glans part.

BACKGROUND ART

According to the prior art, condoms are fitted by breaking the seal of a package, removing the condom body and fitting it on the penis with the fingers, but as the fingers touch the penis and the condom body when it is fitted, there is a problem as to hygiene and whether the condom fits satisfactorily, and if any lubricating oil or powder is used, it adheres to the fingers and must therefore be wiped off. Further, as air enters the condom body, the air must be expelled when it is fitted, which was a nuisance.

A method has been proposed wherein the condom body is provided with a fitting tape having grip parts which is rolled up together with the condom, and when the condom is to be fitted, these grip parts are pulled, e.g., as disclosed in Japanese Patent Publication Hei 2-33765, Japanese Patents Laid-Open Hei 8-56978 and Japanese Utility and Design Patent 3029333. However, the condom body cannot be fitted without removing from its package, so it must again be touched with the fingers.

In another type of condom fitted without removing it from its package with the fingers, and without touching the penis or condom body with the fingers while it is still in its package, a fitting tape is rolled up together with the condom, an extension part is formed beyond this rolled part, and the tip of this part is sealed to the rim of the package, as disclosed in, e.g., Japanese Patent Laid-Open Sho 63-195823, Japanese Patent Publication Hei 3-505173, Japanese Patent Publication Hei 10-510452 and Japanese Patent Laid-Open Hei 11-19110.

However, although these proposals (creative ideas) describe how to fit the condom without touching it with the fingers, it is difficult in practice to fit the condom without touching it. Further, there are a large number of parts and steps involved, the construction is complex and manufacture is difficult. Stability and reliability of steps could not be expected, no consideration was given to maintaining the length of the extension part formed at the tip of the rolled part at a predetermined length, and the condom body unrolled when the package was opened. Due to these manufacturing problems, the product was not commercialized.

If the extension part is short, the fitting tape is pulled and the rolled part is also pulled out when the package is opened, so the condom body is unrolled too much, and if it is fitted in this state, air remains in the glans part. On the other hand, if the extension part is long, although the condom body does not unroll too much when the package is opened, the fitting tape is pulled out too long after opening the package, and the condom body droops down when it is fitted. Hence, it was not easy to fix it on the glans, the fitting stroke was too long, and the user's thigh and hand interfered with each other which made fitting difficult.

The problem common to all these ideas was that, as the tip of the extension part and the rim of the package were sealed simultaneously, the expected length of the extension part easily tended to increase or decrease. Due to the construction of the product, in the steps leading to the final step of the packaging, this could not be resolved and manufacture of the condom was therefore difficult. Moreover in these proposals, no consideration whatever was given to maintaining the length of the extension part within a predetermined range, or to means to achieving that end.

In these condom bodies, there is a sperm retention area in the glans part. Air entered the sperm retention area when the package was opened or the condom was fitted, and remained after the condom was fitted.

There have been proposals for designs which expel the air in the sperm retention part, but in practice, there was still a risk that air would enter when the condom was fitted.

As there is a sperm retention area in the glans part, a considerable amount of air is trapped when the package is opened and the condom body is fitted, and it was difficult to expel this air completely. Due to this accumulation of air, the rubber film of the condom body does not fit closely around the glans, various fatal problems tended to occur such as loss of sexual sensation, a tendency to rupture of the condom body or the condom body easily falling off the penis. To expel the retained air, it was necessary to touch the condom body or the penis with the fingers which gave rise to the above problems or difficulties of usage.

To open the package, it must be split into two equal parts, and as it is generally difficult to split it precisely into two parts, the idea was conceived of providing a seam approximately in the center of the front and rear surfaces. However, it is difficult to make the starting and finishing points of the seam coincide precisely on both the front and rear surfaces during packaging and sealing.

It is therefore an object of this invention to provide a condom wherein an extension part of predetermined length is provided in a fitting tape which is rolled up together with the condom body, i.e., beyond the rolled part. The tip of the extension part is fixed to a predetermined position of the packaging before the package rim is sealed in one piece so that its length does not fluctuate in the packaging step. The package material of the rim of the condom body is then sealed. The condom body can suitably be fixed on the glans without directly touching the penis or condom body, and without unrolling the condom body more than necessary when the package is opened. Hence the condom can be fitted without touching, and furthermore, air does not enter between the glans and the condom when the condom is fitted.

DISCLOSURE OF THE INVENTION

According to this invention, when the condom body is rolled up, a pair of fitting tapes are laterally disposed to the left and right of the condom body. One end of these fitting tapes is disposed in the vicinity of the opening of the condom, the tapes are rolled up together with the condom body along its opposite lateral surfaces, and extension parts are respectively provided in the vicinity of the glans beyond the rolled part of the fitting tapes. After the tips of the extension parts are sealed in one piece with the inner surface of one of the upper package material and lower package material of the package, the other package material is placed over the condom body, and the rims of the package materials are sealed at positions slightly removed from the rim of the condom so as to enclose the condom body. In this way, the extension parts can be maintained at a predetermined length in a step wherein the rolled condom body is made into a sandwich shape by the upper and lower package materials, or in an immediately following step wherein the rim of the condom body is thermocompression bonded.

The seal part between the extension part of the fitting tape and the upper package material is set at about ⅔ of the radius from approximately the outer circumference of the condom body towards the center of the condom. Hence, the length of the extension part is rationally determined within the optimum range from the viewpoint of manufacturing technique, and can be set to the most preferable length.

This resolves the defects inherent in having the extension part of the fitting tape too short, and the disadvantages and difficulties involved in having the extension part too long. As a result, the condom can be suitably fixed on the glans without directly touching the penis or the condom body with the fingers, i.e., a "no touch" fitting is possible.

It is preferred that the glans part of the condom body is fashioned in the shape of a close-cropped monk's head. As there is no sperm retention area in the glans part, there is no risk that air will enter the condom body when it is fitted, and no concern that air will remain. Therefore, the condom is free from the aforesaid problems and disadvantages associated with entry of air.

According to this invention, before sealing the tip of the fitting tape to the package rim in one piece, the extension part is sealed to the upper package material or lower package material of the package. Hence, the extension part need not be eliminated, the shape of the extension part can be maintained, and it can be firmly sealed to the package rim without the tip (excess length) of the fitting tape biting. This also prevents rolling back of excess condom body due to temporary interruptions in pulling the fitting tape, or to sudden pulling under a load.

According to this invention, a notch for opening the package is provided substantially in the center of the upper end, and plural rows of tear lines are provided in the package opening direction substantially in the center of the upper package material or lower package material, or in both, along the notch. As a result, the roughness of the package rim disappears, opening the package is easier, and as tear lines coincide with other parallel tear lines, even if the positioning of a tear line is slightly to the left or right of the predetermined position in the package forming step, smooth opening of the package is enhanced.

BEST MODES FOR CARRYING OUT THE INVENTION

Figure 1:
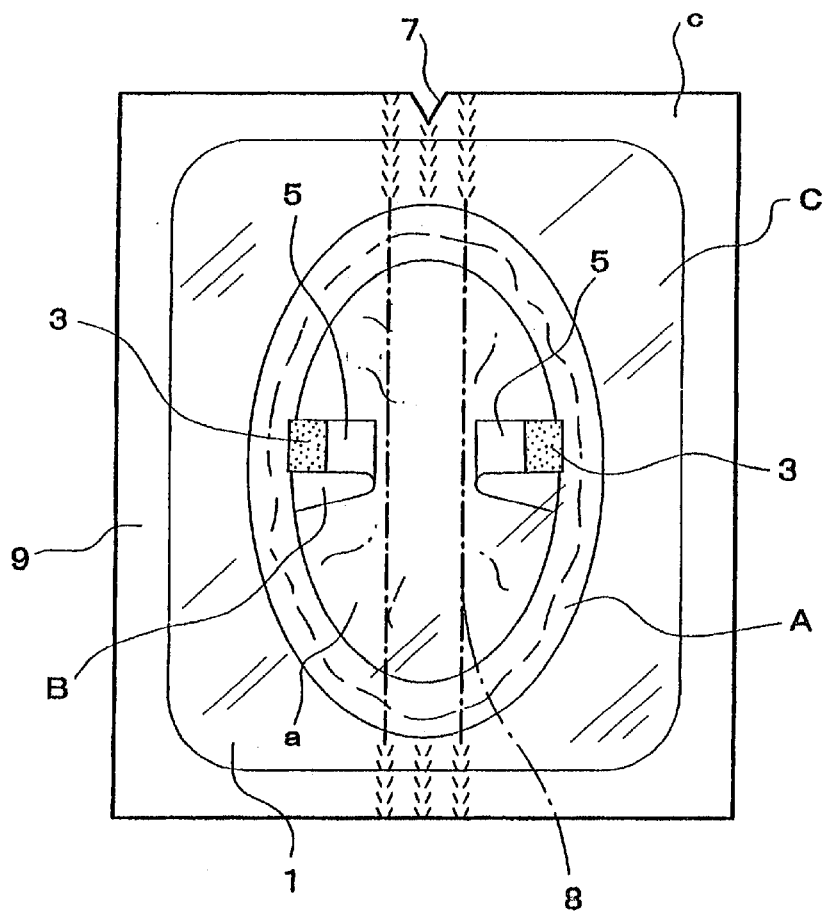
FIG. 1 is a front view of a condom according to this invention.

This invention will now be described in further detail with reference to the drawings.

A condom according to this invention basically comprises a condom body A, a pair of fitting tapes B to the left and right, and a package C. Before a rim c of the package C is sealed 9 by thermocompression bonding, the fitting tape B is sealed 3 to the inner surface of an upper package material 1 or lower package material 2, and the rim c of the package C is then sealed 9 so as to enclose the condom body A.

The condom body A of this invention is formed as an ordinary thin film cylindrical envelope of latex rubber or synthetic resin known in the art in this kind of technical field. There is no restriction on its shape, i.e., there may be a sperm retention area in a glans part a or it may be shaped as a monk's head without a sperm retention part. The monk's head shape is preferred to prevent entry or retention of air, the tip is preferably formed in a flat, curved shape, and a coil is formed in the opening. The coiled width (diameter) is preferably the same as the standard width for products in common use, or a larger diameter than the standard width for products in common use. The pair of fitting tapes B on the left and right are wound together along the opposite lateral surfaces of the condom body A, and these tapes B are housed in the package C such that they are somewhat coiled by winding.

According to this invention, the coiled width (diameter) of the condom body A is preferably effectively equal to that of the standard diameter of products in common use, or a larger diameter than the standard width for products in common use. By making the width a large width of approximately 53–59 mm (diameter approximately 34–38 mm) in comparison to the coiled width of products in common use, which is approximately 51–52 mm (diameter approximately 32–33 mm), idle rotation of the condom on the glans when the condom is fitted is prevented.

Hence, when the diameter of the condom body A is formed larger than the standard diameter common products, the condom can be fitted smoothly without idle rotation on the glans when it is fitted as described hereabove, it fits easier on the glans by making the glans part a flat, and fitting by the fitting tapes B is made still easier.

The flat, curved shape of the tip refers to the relation between the radius of the condom body A and the diameter of the apex of the glans part a, where a flat shape resembling that of a crushed hemisphere is preferable.

The fitting tapes B are tapes of suitable width comprising any flexible, pliable material such as paper or plastic which can be rolled together with the condom body along the opposite lateral faces of the condom body A, e.g., a pair of low density left/right polyethylene tapes of width approximately 10 mm. One end of each of the fitting tapes B is situated in the vicinity of the opening of the condom body A, and the other ends are situated to the left and right along the outer surfaces of the condom so that they can be extended towards the glans part of the condom, and rolled up together with the condom body A. Extension parts 5 are formed in the left and right fitting tapes B beyond a coiled part 4, i.e., in the vicinity of the glans part a, and the tips of the split extension parts 5 are sealed 3 in one piece with the inner surface of one of the upper package 1 or lower package 2 prior to sealing the rim c of the package C by thermo-compression bonding or the like.

Figure 2:
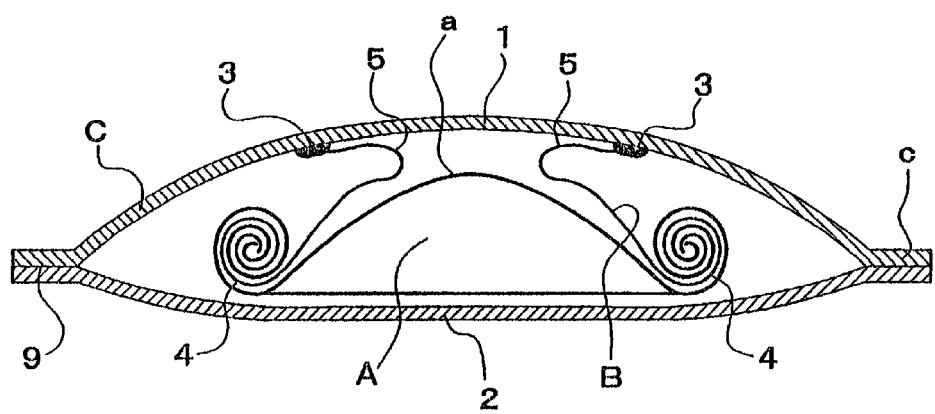
FIG. 2 is an enlarged cross-sectional view of same.
Figure 3:
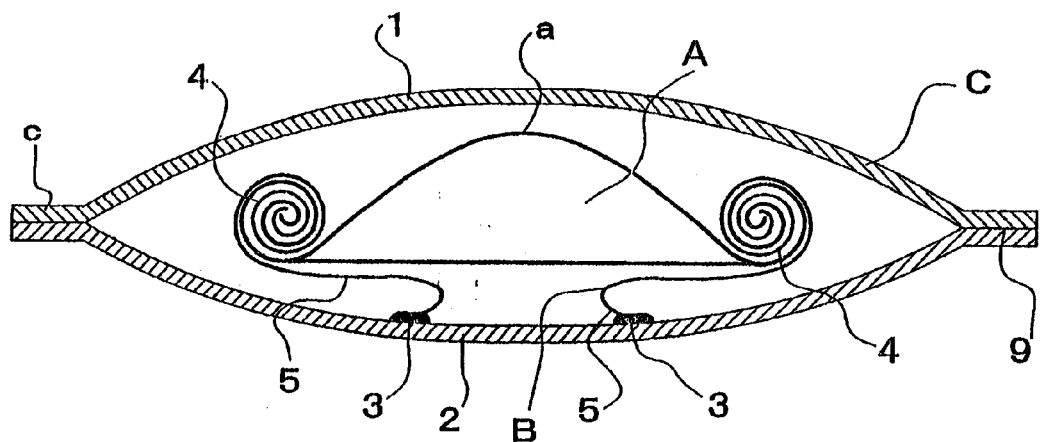
FIG. 3 is an enlarged cross-sectional view of another embodiment.
Figure 4:
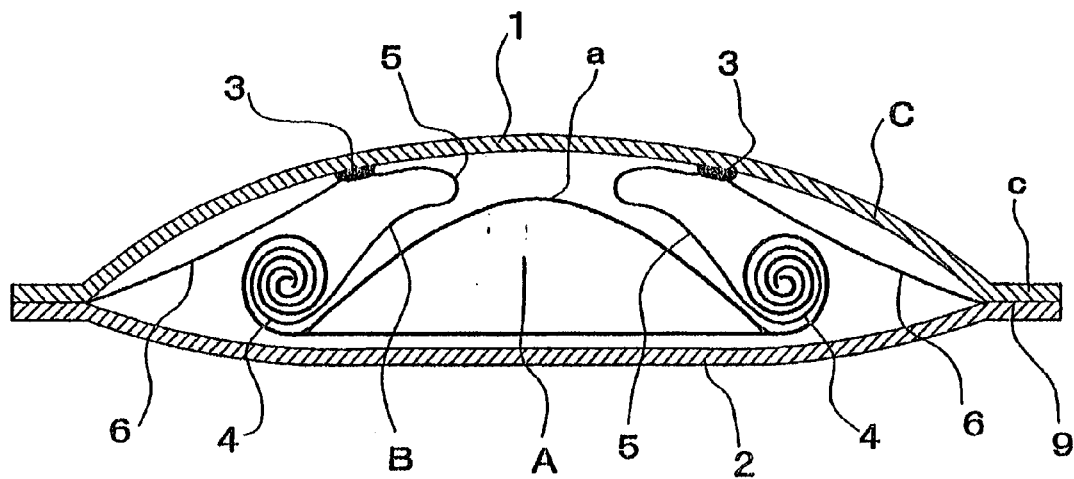
FIG. 4 is an enlarged cross-sectional view of yet another embodiment.
Figure 5:
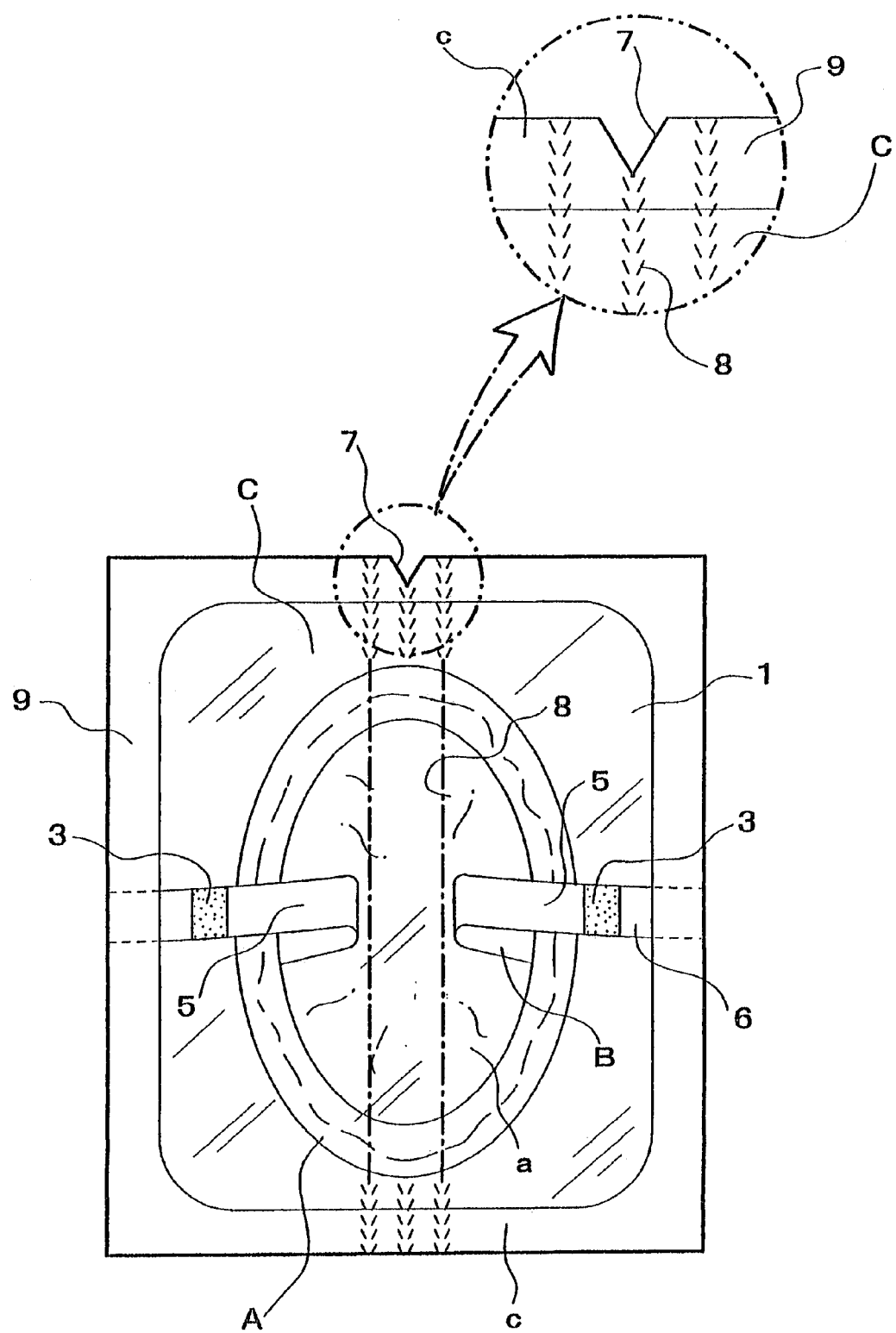
FIG. 5 is a partial cross-sectional view in a front view of another embodiment.
Figure 6:
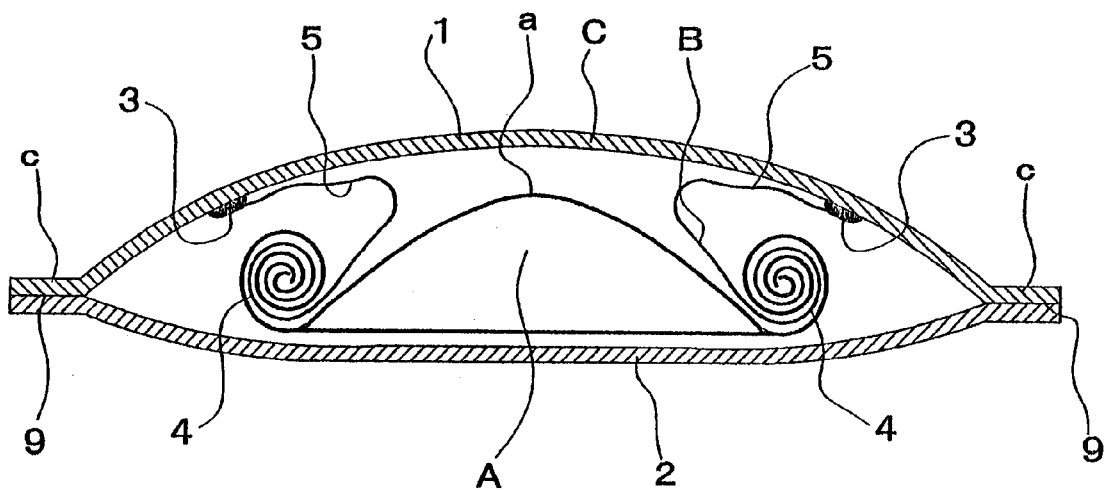
FIG. 6 is an enlarged cross-sectional view of same.
Figure 7:
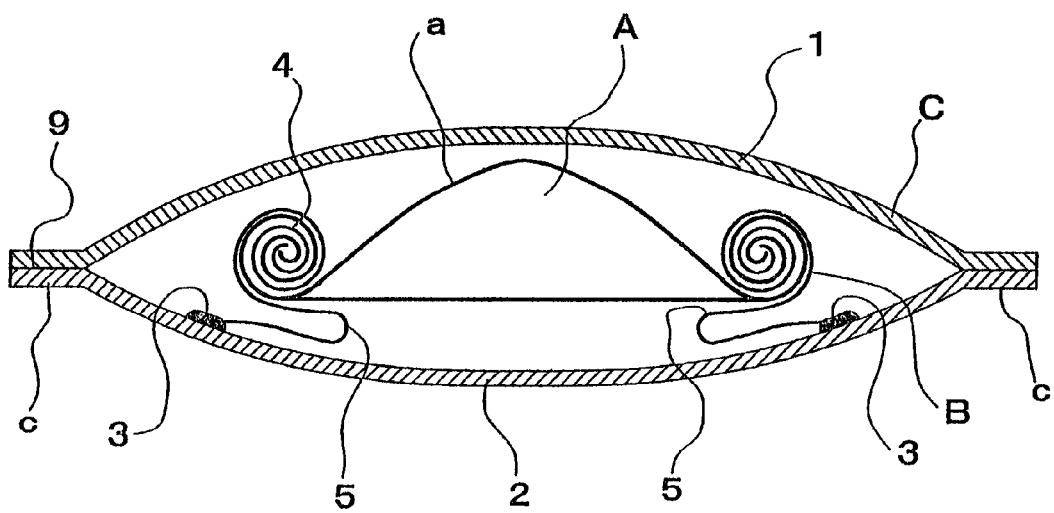
FIG. 7 is an enlarged cross-sectional view of yet another embodiment.
Figure 8:
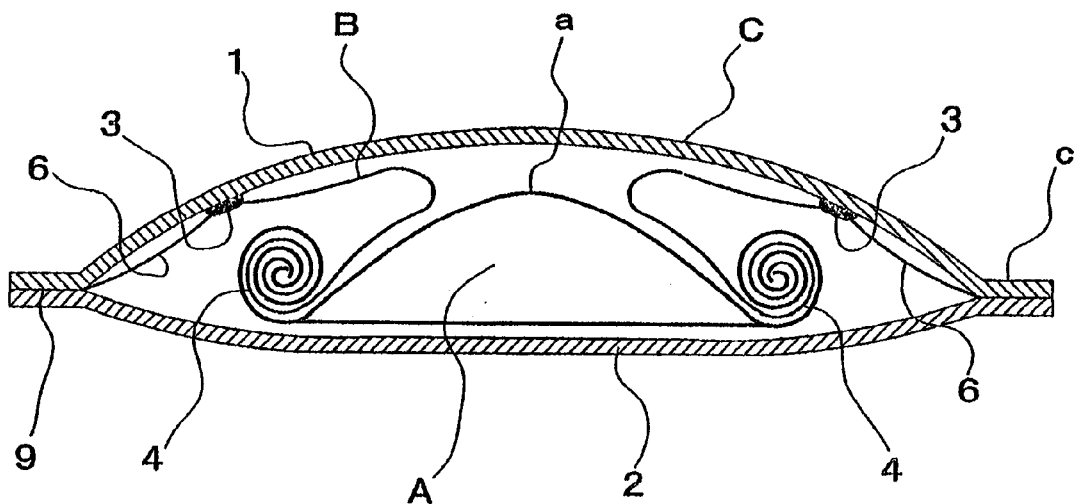
FIG. 8 is an enlarged cross-sectional view of yet another embodiment.

The position of this seal part 3 may be situated more towards the inside (FIG. 2) or outside (FIG. 6) than the outer circumference of the rolled up condom body A, and although it is not the only possible arrangement, the length of the extension part 5 is determined by this seal 3.

After opening the package C, the condom body A is unrolled and fitted by pulling package pieces C' to the left and right of the part where the pair of left and right fitting tapes B used in this invention are sealed (3), downwards. It is therefore indispensable to form the extension parts 5 in a predetermined length in the left and right fitting tapes B so the condom body A does not roll out when the package is opened, and the condom body A does not droop after the package is opened. Therefore, the length of the extension parts 5 is set in a predetermined range, and they are provided equally to the left and right on the front surface or the rolled rear surface in the vicinity of the glans a. The sealing 3 of their tips to the inner surface of one of the upper package 1 and lower package 2 prevents recoiling of the condom body A immediately after the package C is opened, avoids forming an excess extension part in the fitting tapes B, and makes it possible to fit the body A appropriately on the glans without directly touching it with the fingers, i.e., a "no touch" fitting is possible.

Figure 14:
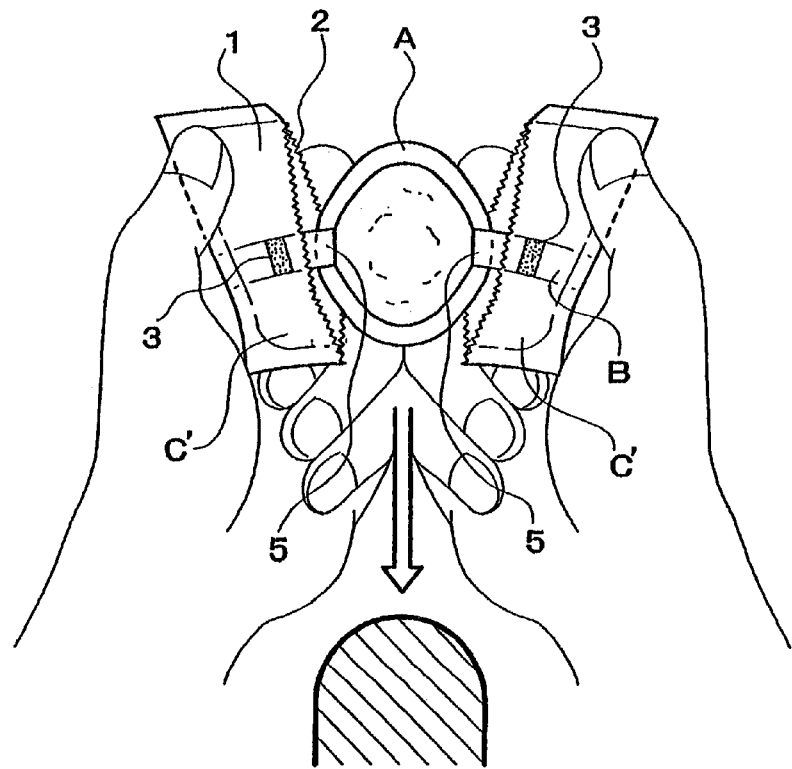
FIG. 14 is a view showing the state of the condom after opening and prior to fitting.
Figure 15:
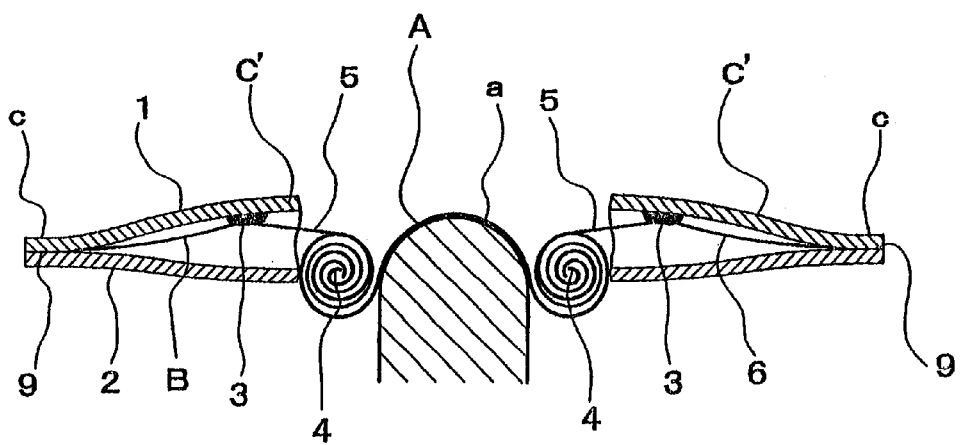
FIG. 15 is a cross-sectional view of the condom when fitting has begun.
Figure 17:
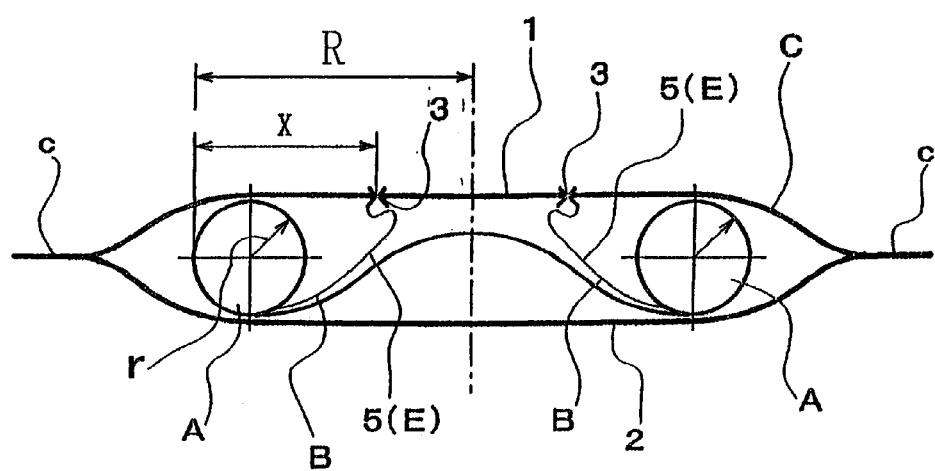
FIG. 17 is a descriptive view related to the length of the extension part.

The length of this extension part 5 is chosen within a suitable range such that, after opening the package C, subject to the condition that the condom body A has been fully exposed from the split package pieces C', the condom body A does not recoil. To prevent the fitting tape B from being excessively drawn out after opening the package C, its length is a length such that the tear ends of the package pieces C' are external tangents to the condom body A )when the condom body A is fitted on the glans in intimate contact therewith, as shown in FIG. 14 and FIG. 15. Its minimum required length is given by the following equations (1), (2) (FIG. 17).

When the seal part 3 is situated further inside than the outer circumference of the condom body A, equation (1) is used, and when it is situated further outside, equation (2) is used.

$$E = r + \pi r + R - x \quad (1)$$

$$E = r + \pi r + R + x \quad (2)$$

where
  R=radius of external diameter of condom body A
  r=radius of rolled part of condom body A in which fitting tape B is also rolled
  x=distance from outer circumference of condom body A to seal part 3
  E=length of extension part 5

The above equations (1), (2) refer to the case where the seal 3 is to the upper package material 1 in a center split, and when the seal part 3 is sealed to the lower package material 2 or when it is unequally divided to the left and right, the length may also be calculated based on them.

The distance x from the outer circumference of the condom body A to the seal part 3 is basically arbitrary, but if a value of x is used where the following inequality (3) is satisfied, the condom body A is exposed from the package C and pulled out further, which is undesirable.

$$r + \pi r + R - x < \sqrt{(x-r)^2 + (2r)^2} \quad (3)$$

The length of the extension part 5 at this time is given by the following equation (4):

$$E = \sqrt{(x-r)^2 + (2r)^2} \quad (4)$$

The extension part 5 becomes longer the nearer the seal part 3 approaches to the rim c of the package C outside the outer circumference of the condom body A, and as excess slack may be trapped in the seal (thermocompression bond) of the rim, the distance x from the outer circumference of the condom body A to this seal part 3 must be a suitable magnitude, and preferably small.

The minimum length occurs when the seal part 3 is sealed to the upper package material 1 at about ⅔ of a radius toward the center (toward the inside) of the condom body A from the outer circumference of the condom body A, and the length E of the extension part 5 at this time satisfies the aforesaid equation (1), which is most preferable.

It is practical to provide the extension part 5 larger than E computed from the above equations (1), (2), but if it is made too large, the condom body A is pulled out too far from the package pieces C' and droops after the package is opened, which gives rise to the above problems. It is therefore best not to adhere strictly to the aforesaid equation, and to allow a tolerance of several mm (e.g., −3 mm to +5 mm) in ½ of the external radius R when the condom body A is rolled up together with the fitting tape B.

By sealing the end of the extension part 5 determined by the aforesaid method in one piece with the inner surface of one of the upper package material 1 or lower package material 2, the extension part 5 can be maintained at a predetermined length, entry of air to the glans part a due to the unrolling of the condom body A immediately after the package C is opened can be prevented, drooping of the condom body A due to excess withdrawal of the fitting tape B can be avoided, and the body A can be appropriately fitted on the glans. Further, the grip hand and thigh of the user do not interfere with each other.

Figure 9:
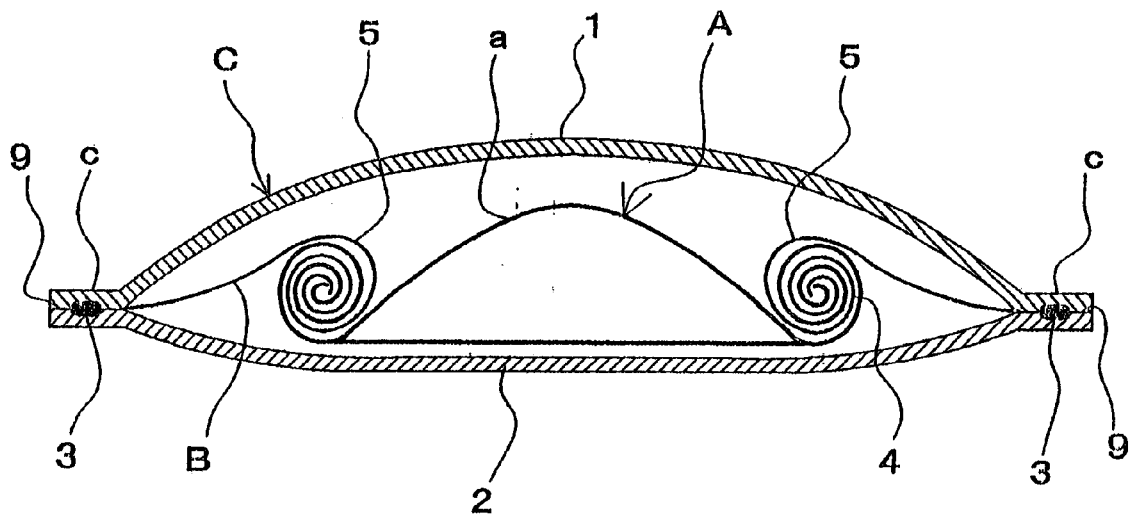
FIG. 9 is an enlarged cross-sectional view of yet another embodiment.

As described above, this extension part 5 is formed by rolling up the fitting tape B together with the condom body A, dividing the fitting tape B to the left and right for predetermined lengths beyond the coiled part 4, i.e., on the front surface in the vicinity of the glans or on the coiled rear surface, and sealing 3 the ends of this divided material to the inner surface of one of the upper package material 1 or lower package material 2 of the package C. This seal part 3 between the fitting tape B and package C is preferably formed by adhesive or thermocompression bonding at a position removed from the peripheral seal between one of the upper package material 1 and lower package material 2 and the fitting tape B, which is a position in the vicinity of the coiled part 4 of the condom body A, prior to sealing 9 the rim c of the upper package material 1 and lower, package material 2. However an extension part of predetermined length can still be maintained even if the position of the seal part 3 is the rim c of the package C as in FIG. 9, and it may also coincide with the position of the seal part 9 of the rim c which is sealed later.

This is because if the seal 9 by thermocompression bonding of the rim c of the upper package material 1 and lower package material 2, and the seal 3 by thermocompression bonding with the fitting tape B, are formed in one operation (simultaneously), the position of the fitting tape B tends to shift, and there tends to be scatter in the length and orientation of the extension part 5, which are not constant. Therefore, the seal 3 between one of the upper package material 1 and lower package material 2 with the fitting tape B beyond the extension part 5 is formed before the seal 9 of the rim c between the upper package material 1 and the lower package material 2. In this way, the length and orientation of the extension part 5 of the fitting tape B are more precise, and the extension part 5 can be tightened before fitting without peeling off the seal 3 when the package is opened.

Due to this seal 3, the end of the fitting tape B can be brought up to the seal 3, and an excess length 6 beyond this may be left as it is or extended to the peripheral part c of the package C, and sealed simultaneously when the seal 9 of the rim c of the package C is formed between the upper and lower package materials 1, 2. Thus, if the excess length and end of the fitting tape B are gripped between the upper package material 1 and lower package material 2 so that the end of the fitting tape B is also firmly sealed in one piece with the package materials 1, 2, a product can be obtained which is temporarily sealed even if the seal 3 is peeled off when the package is opened.

In the package C, the condom body A which is rolled up together with the pair of left and right fitting tapes B is fixed to the upper package material 1 or lower package material 2. To maintain the extension part 5 of predetermined length beyond the rolled part of the fitting tape B, after sealing 3 to the inner surface of one of the upper and lower package materials, the other package material is placed over the condom body A so that the condom body A is sandwiched, and then the seal 9 is formed by thermocompression bonding, etc., of the peripheral part c of the package materials slightly removed from the condom body A so as to enclose the condom body A. An opening notch 7 such as for example a V-shaped notch or a straight indent is provided in the center part of the rim, and plural rows of tear lines 8 for opening ate formed substantially in the center, of one or both of the upper and lower package materials.

The package materials 1, 2 comprise films or package materials having thermocompression bonding properties known in the art in this kind of technical field. For example, the upper package material 1 comprises a transparent plastic film and the lower package material 2 comprises an aluminum foil package material wherein a sealant is laminated, but the aluminum foil package material 1 may also be an aluminum foil package material wherein a sealant is laminated. Too much opening of the package can be prevented, and fitting is assisted, by displaying the position on the upper package material 1 where the package is to be gripped (held) by both hands, and the left and right thumbs are to be placed when the package is opened, or by printing instructions to be used when the package is opened. Regarding the position of the thumbs, the tips of the left and right thumbs, or the left and right thumbs, are displayed substantially parallel so that the package C is held by the left and right hands, the notch 7 is gradually opened, and the thenars (or bases) of the left and right thumbs come in contact before the package is torn open to the end.

The sealant of the upper and lower package materials 1, 2 and the fitting tape B is preferably comprised of a polyolefine having good heat seal properties (polyethylene, random polypropylene or EVA), polyethylene being particularly convenient.

The tear line 8 is generally straight like a "seam", but rectilinearity may be conferred by providing a slanting, thin part in the shape of the Japanese letter "ha" or an inverted Japanese letter "ha" in the opening direction substantially in the center of one or both of the package materials on the front and rear surfaces by die pressing or embossing, as shown in the drawings. This tear line, which is used for opening the package, is a thin part which is formed in the shape of the Japanese letter "ha" or an inverted Japanese letter "ha" by applying a predetermined pressure from the front and rear surfaces of the package materials 1, 2 in the shape of the Japanese letter "ha" or an inverted Japanese letter "ha", as described above. By forming plural (e.g. 2–7) rows of the tear lines 8, the package can be opened efficiently without any shift in the tear direction (opening direction) along the notch 7 in the center part of the upper end of the package C even if the starting and finishing points of this opening tear line on the front and rear surfaces do not perfectly coincide.

This tear line is not limited to the shape of the Japanese letter "ha" or an inverted Japanese letter "ha". Rectilinearity can be conferred in the way the package is opened and ease of opening can be enhanced by forming the tear line in a staggered shape as a combination of slanting lines and a straight line, such as for example in the shape of a letter "Y" or an inverted letter "Y", or a shape wherein a slanting line is slightly shifted up or down so that the extrapolation of one slanting line intersects with the other slanting line.

Industrial Applicability

Next, the method of using the condom according to the invention will be described.

Figure 10:
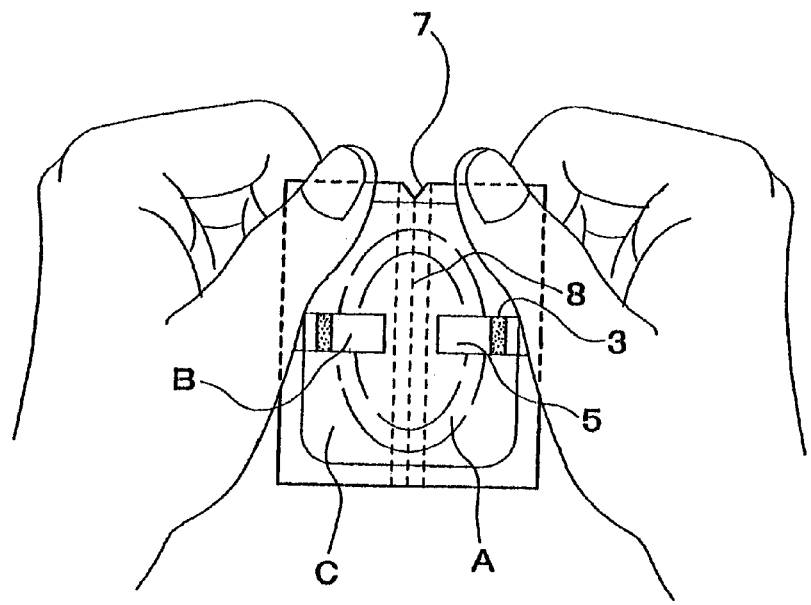
FIG. 10 is a descriptive view of the package when it is first opened.
Figure 11:
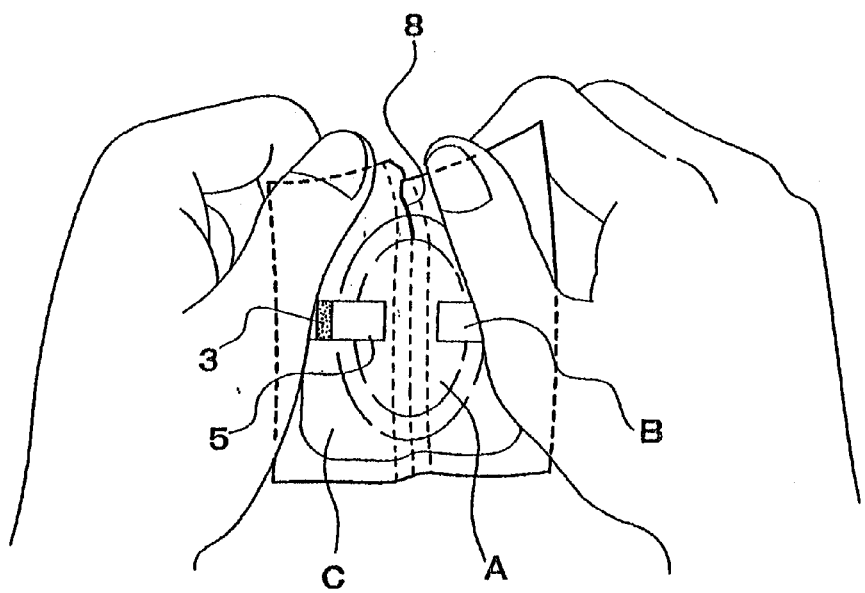
FIG. 11 is a descriptive view showing the state of the package at a later time during opening.
Figure 12:
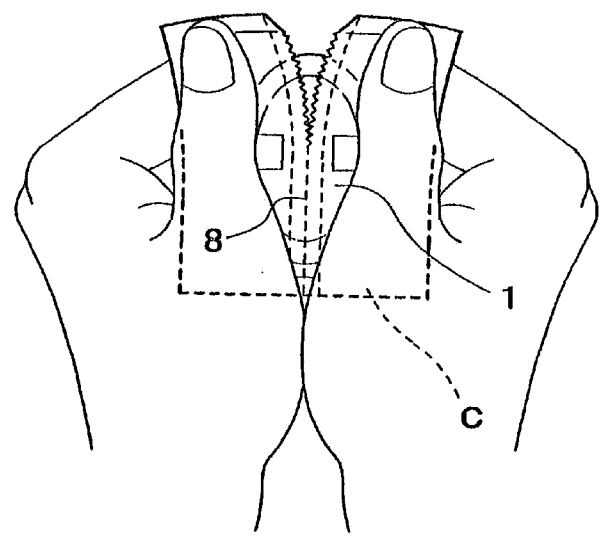
FIG. 12 is a descriptive view showing the state of the package at a later time during opening.
Figure 13:
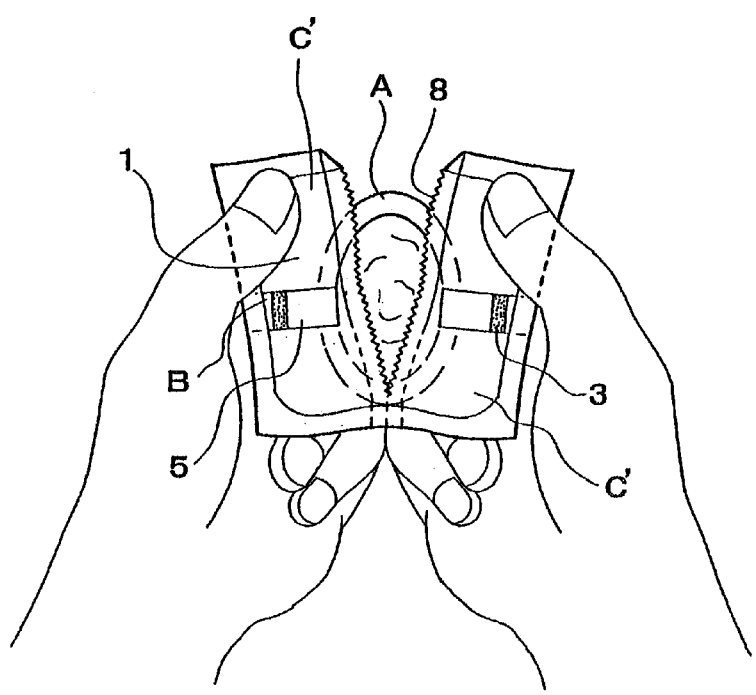
FIG. 13 is a descriptive view showing the state of the package at a later time during opening.
Figure 16:
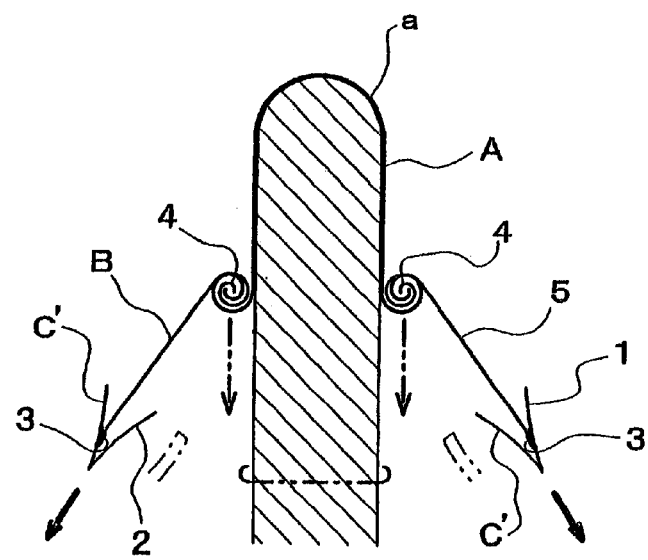
FIG. 16 is a descriptive view showing the state when the fitting tape is pulled out.

As shown in FIG. 10, the package C is gripped with both hands by placing the thumbs in the thumb grip positions displayed on the front surface of the package C and placing the four fingers of the left and right hands on the rear surface, the package is gradually torn open from the notch 7 to the end along the tear line 8 with the little fingers of the left and right hands still in place (FIG. 11), the thenars (bases) of the thumbs of both hands come in contact and the contact parts are gradually separated (FIG. 12). The parts are completely separated up to the end of the package C, the separated package pieces C' are pulled apart while they are still gripped and the extension parts 5 of the fitting tape B are pulled out so that the condom body A does not roll back. Opening is temporarily stopped in the state shown in FIG. 14, the condom body A is placed in intimate contact with the glans (FIG. 15), and the package pieces C', which are split into two, are pulled toward the base of the penis. The fitting tape B and condom body A are then rolled back (FIG. 16) so that it is completely fitted over the penis with the fitting tape B peeled away from the condom body A.

What is claimed is:

1. A condom, comprising a coiled condom body (A), upper and lower package materials (1), (2) of a package (C) being sealed at a rim of or slightly removed from the coiled condom body (A) so as to enclose the condom body (A), a pair of left and right fitting tapes (B) are disposed on opposite lateral surfaces of the condom body (A) when the condom body (A) is rolled up, one end of the fitting tape (B) is positioned in the vicinity of an opening of the condom body (A) and the fitting tape (B) is rolled up together with the condom body (A) along a lateral surface of the condom body (A), extension part (5) of the fitting tape (B) being in the vicinity of a glans part beyond a coiled part (4) of the fitting tapes (B), a tip of the extension part (5) being sealed (3) with the inner surface of only one of the upper and lower package materials (1), (2) at a point spaced from the seal (9) between the upper and lower package materials (1), (2).

2. A condom as defined in claim 1, wherein the seal part (3) of the extension part (5) of the fitting tape (B) to the upper package material (1) is set within approximately ⅔ of the radius towards the center of the condom body (A) from approximately the outer circumference of the condom body (A).

3. A condom as defined in claim 2, wherein a notch (7) is provided substantially in the center of the upper end when the package (C) is opened, and plural rows of tear lines (8) are formed in the opening direction substantially in the center of one or both of the upper package material (1) and lower package material (2) along the notch (7).

4. A condom as defined in claim 1, wherein a notch (7) is provided substantially in the center of the upper end when the package (C) is opened, and plural rows of tear lines (8) are formed in the opening direction substantially in the center of one or both of the upper package material (1) and lower package material (2) along the notch (7).

5. A condom, comprising a coiled condom body (A), upper and lower package materials (1), (2) of a package (C) being sealed at a rim of or slightly removed from the coiled condom body (A) so as to enclose the condom body (A), a pair of left and right fitting tapes (B) are disposed on opposite lateral surfaces of the condom body (A) when the condom body (A) is rolled up, one end of the fitting tape (B) is positioned in the vicinity of an opening of the condom body (A) and the fitting tape (B) is rolled up together, with the condom body (A) along a lateral surface of the condom body (A), extension part (5) of the fitting tape (B) being in the vicinity of a glans part beyond a coiled part (4) of the fitting tapes (B), rims of the two package materials (1), (2) are sealed (9) together after a tip of the extension part (5) being sealed (3) with the inner surface of only one of the upper and lower package materials (1), (2) at a point spaced from the seal (9) between the upper and lower package materials (1), (2).

6. A condom as defined in claim 5, the seal part (3) of the extension part (5) of the fitting tape (B) to the upper package material (1) is set within approximately ⅔ of the radius towards the center of the condom body (A) from approximately the outer circumference of the condom body (A).

7. A condom as defined in claim 6, wherein a notch (7) is provided substantially in the center of the upper end when the package (C) is opened, and plural rows of tear lines (8) are formed in the opening direction substantially in the center of one or both of the upper package material (1) and lower package material (2) along the notch (7).

8. A condom as defined in claim 5, wherein a notch (7) is provided substantially in the center of the upper end when the package (C) is opened, and plural rows of tear lines (8) are formed in the opening direction substantially in the center of one or both of the upper package material (1) and lower package material (2) along the notch (7).

9. A condom wherein a pair of left and right fitting tapes (B) are disposed on opposite lateral surfaces of a condom body (A) when the condom body (A) is rolled up, one end of the fitting tape (B) is positioned in the vicinity of an opening of the condom body (A) and the fitting tape (B) is rolled up together with the condom body (A) along a lateral surface of the body (A), extension parts (5) are provided in the vicinity of the glans part beyond a coiled part (4) of the fitting tape (B), the tip of the extension part (5) is sealed (3) in one piece with the inner surface of one of an upper package material (1) and a lower package material (2) of a package (C), the other package material is placed over the coiled condom body (A), rims of the two package materials (1), (2) are sealed (9) at a rim of or slightly removed from the coiled condom body (A) so as to enclose the condom body (A), and the seal part (3) of the extension part (5) of the fitting tape (B) to the upper package material (1) is set within approximately ⅔ of the radius towards the center of the condom body (A) from approximately the outer circumference of the condom body (A).

10. A condom as defined in claim 9, wherein a notch (7) is provided substantially in the center of the upper end when the package (C) is opened, and plural rows of tear lines (8) are formed in the opening direction substantially in the center of one or both of the upper package material (1) and lower package material (2) along the notch (7).

11. A condom wherein a glans part of a condom body (A) is formed in the shape of a close-cropped monk's head, a pair of left and right fitting tapes (B) are disposed on opposite lateral surfaces of a condom body (A) when a condom body (A) is rolled up, one end of the fitting tape (B) is positioned in a vicinity of an opening of the condom body (A) and the fitting tape (B) is rolled up together with the condom body (A) along a lateral surface of the body (A), the other end of the tape is split into two extension parts (5) respectively provided in the vicinity of the glans part, their tips are sealed (3) in one piece with the inner surface of one of an upper package material (1) and a lower package material (2) of a package (C), the other package material is placed over the coiled condom body (A), rims of the two package materials (1), (2) are sealed (9) at the rim of or slightly removed from the coiled condom body (A) so as to enclose the condom body (A), and the seal part (3) of the extension part (5) of the fitting tape (B) to the upper package material (1) is set within approximately ⅔ of the radius towards the center of the condom body (A) from approximately the outer circumference of the condom body (A).

12. A condom as defined in claim 11, wherein a notch (7) is provided substantially in the center of the upper end when the package (C) is opened, and plural rows of tear lines (8) are formed in the opening direction substantially in the center of one or both of the upper package material (1) and lower package material (2) along the notch (7).

* * * * *